United States Patent
Komp

(10) Patent No.: US 11,922,581 B2
(45) Date of Patent: Mar. 5, 2024

(54) SYSTEMS AND METHODS OF CONTROLLING AN OPERATING ROOM DISPLAY USING AN AUGMENTED REALITY HEADSET

(71) Applicant: Covidien LP, Mansfield, MA (US)

(72) Inventor: John W. Komp, Dillon, CO (US)

(73) Assignee: Coviden LP, Mansfield, MA (US)

( * ) Notice: Subject to any disclaimer, the term of this patent is extended or adjusted under 35 U.S.C. 154(b) by 0 days.

(21) Appl. No.: 17/196,344

(22) Filed: Mar. 9, 2021

(65) Prior Publication Data

US 2021/0350624 A1 Nov. 11, 2021

Related U.S. Application Data

(60) Provisional application No. 63/022,219, filed on May 8, 2020.

(51) Int. Cl.
| | |
|---|---|
| G06T 19/00 | (2011.01) |
| G02B 27/00 | (2006.01) |
| G02B 27/01 | (2006.01) |
| G06F 3/01 | (2006.01) |
| G06F 3/0482 | (2013.01) |
| G06F 3/04855 | (2022.01) |

(52) U.S. Cl.
CPC ........ G06T 19/006 (2013.01); G02B 27/0093 (2013.01); G02B 27/017 (2013.01); G06F 3/013 (2013.01); G06F 3/0482 (2013.01); G06F 3/04855 (2013.01); G02B 2027/0187 (2013.01)

(58) Field of Classification Search
CPC .............. G06T 19/006; G02B 27/0093; G02B 27/017; G06F 3/013; G06F 3/0482; G06F 3/04855

USPC ........................................................ 345/633
See application file for complete search history.

(56) References Cited

U.S. PATENT DOCUMENTS

| | | | | |
|---|---|---|---|---|
| 10,580,325 | B2* | 3/2020 | Bronstein | ............. G06T 19/006 |
| 2015/0206321 | A1* | 7/2015 | Scavezze | ........... G02B 27/0172 |
| | | | | 345/633 |
| 2016/0025971 | A1* | 1/2016 | Crow | ...................... G06F 1/163 |
| | | | | 345/156 |

(Continued)

FOREIGN PATENT DOCUMENTS

| | | | |
|---|---|---|---|
| BR | 0013237 | A | 7/2003 |
| BR | 0116004 | A | 6/2004 |

(Continued)

OTHER PUBLICATIONS

Extended European Search Report issued in corresponding European Patent Application No. 21172891 dated Oct. 12, 2021, 16 pages.

*Primary Examiner* — Hai Tao Sun

(74) *Attorney, Agent, or Firm* — Weber Rosselli & Cannon LLP

(57) ABSTRACT

Augmented reality (AR) systems and methods involve an interactive head-mounted device (HMD), an external display, and a medical image computer, which is in communication with the HMD and the external display. The external display displays one or more planes of a medical image or a 3D model provided by the medical image computer. A user wearing the HMD may manipulate a medical image or 3D model displayed on the external display by focusing the user's gaze on a control object and/or a portion of a medical image or 3D model displayed on a display of the interactive HMD.

16 Claims, 8 Drawing Sheets

(56) References Cited

U.S. PATENT DOCUMENTS

| | | | |
|---|---|---|---|
| 2017/0115728 A1* | 4/2017 | Park | G02B 27/0093 |
| 2017/0151034 A1* | 6/2017 | Oda | A61B 1/00048 |
| 2018/0032130 A1* | 2/2018 | Meglan | G02B 27/0093 |
| 2019/0005848 A1 | 1/2019 | Kilroy et al. | |
| 2019/0011703 A1 | 1/2019 | Robaina et al. | |
| 2020/0004328 A1 | 1/2020 | Blume et al. | |
| 2020/0069388 A1 | 3/2020 | Bailey | |
| 2020/0188028 A1* | 6/2020 | Feiner | G06F 3/013 |
| 2020/0352427 A1 | 11/2020 | Deyanov | |
| 2020/0383750 A1 | 12/2020 | Kemp et al. | |

FOREIGN PATENT DOCUMENTS

| | | |
|---|---|---|
| MX | PA03005028 A | 1/2004 |
| MX | 225663 B | 1/2005 |
| MX | 226292 | 2/2005 |
| MX | 246862 B | 6/2007 |
| MX | 265247 | 3/2009 |
| MX | 284569 B | 3/2011 |
| WO | 2019040493 A1 | 2/2019 |

* cited by examiner

SYSTEMS AND METHODS OF CONTROLLING AN OPERATING ROOM DISPLAY USING AN AUGMENTED REALITY HEADSET

CROSS-REFERENCE TO RELATED APPLICATION

This application claims the benefit of and priority to U.S. Provisional Patent Application No. 63/022,219, filed May 8, 2020, the entire disclosure of which is incorporated by reference herein.

FIELD

This disclosure relates to the field of operating room equipment, and particularly to controlling an operating room display using an augmented reality headset.

BACKGROUND

During surgical procedures, patient scans (e.g., computed tomography (CT) scans, magnetic resonant imaging (MRI) scans, or positron emission tomography (PET) scans) are commonly displayed on a monitor in the operating room (OR) to guide the surgeon in performing the surgical procedures, e.g., to guide a catheter tip to a target identified in the patient scans. Oftentimes, the surgeon needs to manipulate a patient scan shown on the OR monitor, e.g., move between slices of the patient scan or center a target in the display in order better view the relevant portions of the patient's anatomy. When the surgeon is scrubbed in, it is difficult for the surgeon to manipulate a patient scan in the OR monitor to focus on a relevant portion of the patient volume while performing a surgical procedure. Therefore, there is a need for methods and systems allowing a surgeon to manipulate patient scans on a display without having to perform too many steps in addition to the steps of the surgical procedure.

SUMMARY

The techniques of this disclosure generally relate to controlling an operating room display using an augmented reality headset so that a scrubbed-in surgeon can easily, accurately, and sterilely manipulate patient scan information displayed on the operating room display.

In one general aspect, this disclosure features a method that includes displaying scan information on an external display, displaying at least one plane of scan information on a display of an augmented reality (AR) head-mounted device (HMD) based on the scan information displayed on the external display, monitoring a location of a focus of a user's gaze, and updating the scan information on the external display based on monitored movement of the location of the focus of the user's gaze. Other implementations of this aspect include corresponding computer systems, apparatus, and computer programs recorded on one or more computer storage devices, each configured to perform the actions of the method.

Implementations may include one or more of the following features. The method may include displaying a control object outside the scan information displayed on the AR HMD; detecting that the user's gaze is focused on the control object; in response to detecting that the user's gaze is focused on the control object, determining that the user's gaze satisfies a predetermined condition; and in response to determining that a characteristic associated with the user's gaze satisfies a predetermined condition, recording selection of the control object. Determining that a characteristic associated with the user's gaze satisfies a predetermined condition may include determining that the user's gaze is maintained for greater than a predetermined period. Determining that a characteristic associated with the user's gaze satisfies a predetermined condition may include determining that the user blinks for greater than a predetermined period.

The method may include in response to recording the selection of the control object, displaying at least one plane of scan information in place of the control object displayed on the display of the AR HMD. The control object may be a virtual joystick, a scrollbar, a button, or a selectable icon. The control object may be a slider of a scrollbar. The method may include detecting movement of the user's gaze to another position on the scrollbar and displaying a plane of scan information corresponding to the another position on the scrollbar. The method may include continuously displaying at least one plane of scan information on the display of the AR HMD. The at least one plane of scan information may be displayed on the display of the AR HMD based on the determined number of planes of scan information. The at least one plane of scan information may be displayed on the display of the AR HMD based on the determined number of planes of scan information.

The scan information may include computed tomography (CT) scan information, magnetic resonant imaging (MRI) scan information, positron emission tomography (PET) scan information, or any combination thereof. The method may include detecting that the user's gaze is focused on a plane of scan information and, in response to detecting that the user's gaze is focused on a plane of scan information, highlighting the plane of scan information and displaying control objects associated with the highlighted plane of scan information. Highlighting the plane of scan information may include changing a fill color, a fill pattern, a border color, or a border style of the plane of scan information. Displaying control objects associated with the highlighted plane of scan information may include displaying movement direction control buttons on opposite sides of the highlighted plane of scan information. The movement direction control buttons may include up and down control buttons or forward and backward control buttons.

The method may include detecting that the user's gaze is focused on a control object and, in response to detecting that the user's gaze is focused on the control object, determining selection of the control object and moving the highlighted plane of scan information in the direction associated with the selected control object. The highlighted plane of scan information may be moved at a predetermined rate. The method may include determining a length of time of detecting that the user's gaze is focused on a control object, and increasing a movement rate at which the highlighted plane of scan information is moved based on the determined length of time. Increasing the movement rate may include increasing the movement rate linearly or in predetermined steps. Displaying scan information may include displaying a three-dimensional (3D) model constructed based on medical scans. The method may include detecting that the user's gaze is focused on a portion of the 3D model and, in response to detecting that the user's gaze is focused on the portion of the 3D model, displaying a plane of scan information corresponding to the portion of the 3D model.

In another general aspect, this disclosure features a method that includes receiving scan information from a medical image computer in communication with an external display; displaying at least one plane of the scan information; displaying at least one control object associated with the at least one plane of scan information; detecting that a user's gaze is focused on the at least one control object; and, in response to detecting that the user's gaze is focused on the control object, transmitting a first control message to the medical image computer to change the display of the scan information on the external display. The method also includes receiving a second control message from the medical image computer to change the display of the at least one plane of the scan information, and changing the display of the at least one plane of scan information based on the second control message. Other implementations of this general aspect include corresponding computer systems, apparatuses, and computer programs recorded on one or more computer storage devices, each configured to perform the actions of the method.

Implementations may include the following feature. The control message may include instructions to change a position, an orientation, or a size of the scan information, or instructions to hide or show at least a portion of the scan information.

In another general aspect, this disclosure features a system that includes an operating room monitor that displays scan information and an interactive head-mounted device in communication with the operating room monitor. The interactive head-mounted device includes an optical assembly that displays medical images and enables viewing of at least a portion of a surrounding environment. The system also includes an eye tracking device that tracks a location of a focus of a user's gaze, a processor in communication with the optical assembly and the eye tracking device, a memory that stores an application, which, when executed by the processor, causes the processor to: display scan information on the operating room monitor; display at least one plane of scan information on the interactive head-mounted device based on the scan information displayed on the operating room monitor; monitor a location of a focus of a user's gaze; update the scan information on the operating room monitor based on monitored movement of the location of the focus of the user's gaze; determine that the scan information is changed on the operating room monitor; and in response to determining that the scan information is changed on the operating room monitor, update the at least one plane of scan information displayed on the interactive head-mounted device based on the scan information changed on the operating room monitor.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

Various exemplary aspects are illustrated in the accompanying figures. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. The figures are listed below.

DETAILED DESCRIPTION

Figure 1:
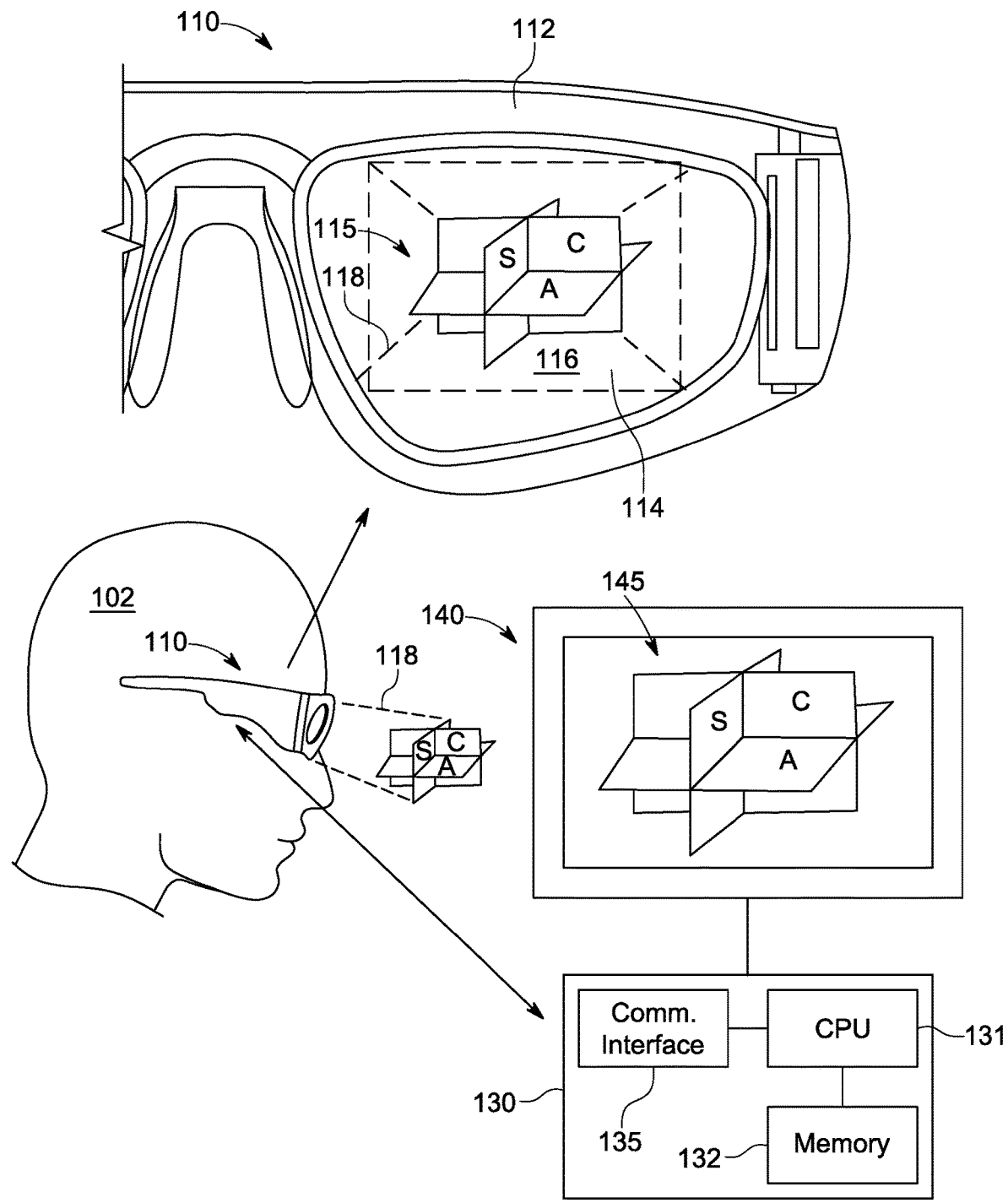
FIG. 1 is a schematic block diagram of a system configured for use with the methods of the disclosure.

During surgical procedures, patient scans (e.g., computed tomography (CT) scans, magnetic resonant imaging (MRI) scans, or positron emission tomography (PET) scans) or a three-dimensional (3D) model constructed based on the patient scans are commonly displayed on a display in the operating room (OR) (e.g., the external monitor 140 of FIG. 1). Depending on the method used to display patient scans or a 3D model, there may be one plane (e.g., the Axial (A) plane 202 graphically illustrated in FIG. 2A) shown or there may be additional planes (e.g., the Coronal (C) plane 204 and the Sagittal (S) plane 206 graphically illustrated in FIG. 2A) shown.

Once the surgeon is scrubbed in, the surgeon may not be able to easily, accurately, and sterilely manipulate patient scan information displayed on the OR display. For example, the OR display may be covered with a sterile bag, which may affect touchscreen capabilities and the clarity of the OR display as seen through the sterile bag, making it difficult for the surgeon to accurately or properly manipulate a touchscreen of the OR display to, among other things, focus on a relevant portion of a patient volume. The surgeon may have three options: use a sterilizable pointing device (e.g. trackball, joystick), scrub out and manipulate the OR display themselves, or direct a non-sterile member of the surgical team to adjust the OR display. However, these options have the following drawbacks: sterilizable interfaces are not always available, the surgeon must scrub in after scrubbing out and manipulating the OR display thereby prolonging the surgery, and providing verbal directions to the non-sterile member of the surgical team may be difficult and frustrating for the surgeon depending on the knowledge and experience of the non-sterile member of the surgical team.

As illustrated in FIG. 1, an aspect of this disclosure is to give the clinician 102, e.g., a surgeon, direct, hands-free control of how one or more planes of a patient scan 145 are displayed on the external monitor 140 in the operating room. The clinician 102 wears an Augmented Reality (AR) headset 110 or any other suitable head-mounted device (HMD) having a frame 112, which incorporates eye tracking hardware (e.g., eye tracking sensors) and which supports a lens 124 including a see-through headset display 116 for displaying a projection 118 of a patient scan 115. The patient scan 115 may be a modified version (e.g., a lower resolution version) of the patient scan 145 so that the patient scan 115 can be displayed as a projection 118 on the see-through headset display 116 of the AR headset 110.

A headset computer (e.g., the headset computer 310 of FIG. 3), which is integrated into the AR headset 110, monitors the current location or movement of the focus of the surgeon's gaze, updates the patient scan 115 on the headset display 116 based on the current location or movement of the focus of the surgeon's gaze, and provides scan display information, which includes display parameters associated with the updated patient scan 115, to a communications interface 135 of the external medical image computer 130. Then, a processor 131 executes instructions stored in a memory 132 of the external medical image computer 130, to cause the medical image computer 330 to change the displayed patient scan 145 based on scan display information received from the AR headset 110.

The headset computer may employ any suitable method of placing the projection 118 of scan information, e.g., the patient scan 115, which does not obstruct the surgical field or otherwise interfere with a clinician's ability to accurately view the surgical field. In one example method, the projection 118 of the patient scan 115 is continuously displayed at a fixed position and/or orientation relative to the AR headset 110. For example, if the projection 118 of the patient scan 115 is displayed in the upper right corner of the see-through headset display 116, the projection 118 of the patient scan 115 is continuously displayed in the upper right corner of the see-through headset display 116 no matter the position and/or orientation of the AR headset 110.

In another example method, the projection 118 is anchored to a fixed location so that the user wearing the AR headset 110 must look in a general direction of the fixed location to see the projection 118. The AR headset 110 may include one or more sensors for determining the orientation of the AR headset 110. Thus, when the user wearing the AR headset 110 turns her head away from the fixed location, the projection moves out of the user's view through the AR headset 110. And when the user orients her head towards the fixed location, the projection 118 returns to the user's view through the AR headset 110. In one aspect, an icon may be displayed at the edge of the user's view that points in the direction of the projection 118 as an aid in relocating the projection 118 when it is outside the user's current view.

Figure 2A:
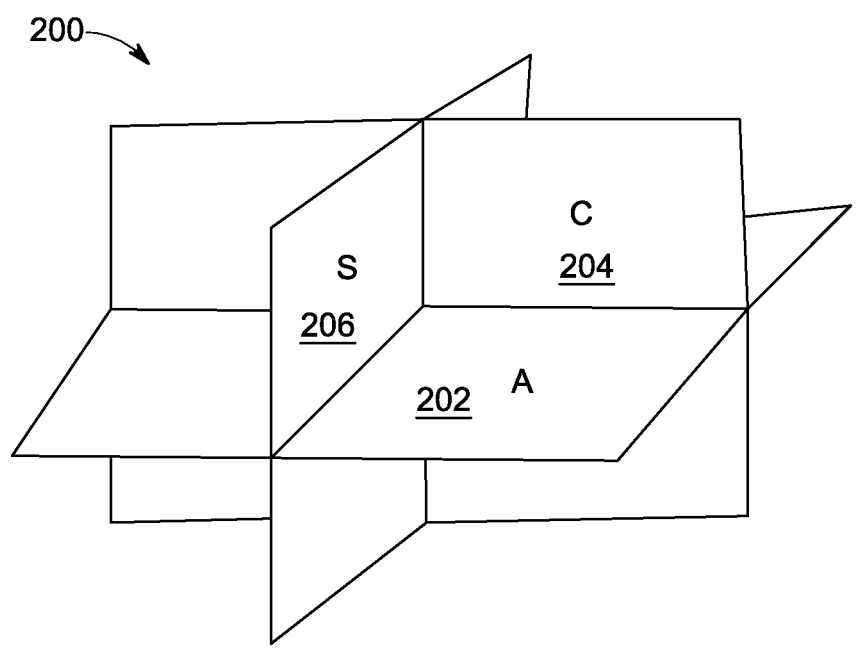
FIGS. 2A-2C are graphical diagrams of displayed scan information according to aspects of the disclosure.

In an aspect of the disclosure, the headset display 116 may show one or more icons or buttons for controlling the display of scan information on the headset display 116 and on the external monitor 140. The one or more icons may be shown towards an edge of the display 116, outside the primary view to avoid occluding the surgeon's view of the surgical site. According to an example of a display method, the one or more icons includes an icon or other symbol that represents the full display illustrated in FIG. 2A, e.g., a thumbnail image. Then, when the eye tracker 322 detects that the surgeon's gaze is focused on the icon, the icon is replaced with the full display of FIG. 2A. In some aspects, the eye tracker 322 detects a user selection of an icon by detecting either a long pause of the user's eye focus on the icon or a long blink. Alternatively, FIG. 2A can be continuously displayed and the icon or other symbol that represents the full display shown in FIG. 2A is not displayed. The number of planes of the patient scan 115 displayed on the headset display 116 may be based on information from the medical image computer 130 so as to reflect those planes either currently displayed on the OR monitor or that are available but not currently being displayed. In aspects, the headset display 116 may display one or more hide/show icons, which, when selected by a user's gaze, causes one or more planes of the patient scan 115 or a 3D model to be shown or hidden.

Figure 2B:
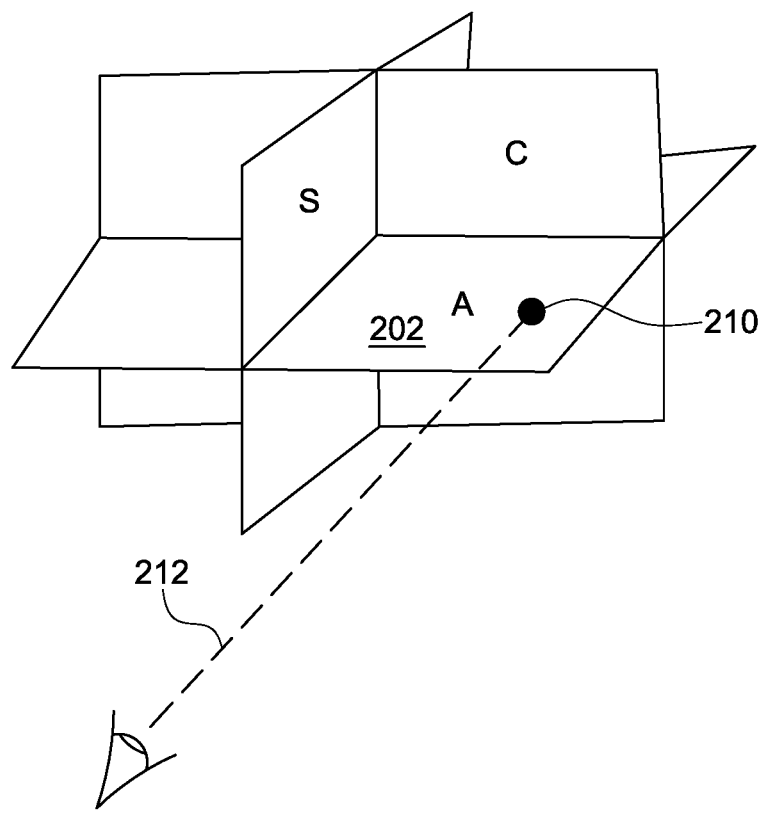

After the patient scan 200 illustrated in FIG. 2A is displayed on the display of the AR headset 110, the surgeon selects the plane (e.g., plane 202, 204, or 206) to use for adjusting the patient scan 200. As further illustrated by FIGS. 2B and 2C, when the surgeon's view or gaze 212 is focused on a point 210 on the axial plane 202 for a predetermined period, the axial plane 202 is highlighted 224, indicating that the axial plane 202 has been selected by the surgeon. In other aspects, a plane may be selected by detecting a long pause in the motion of the focus of the surgeon's gaze 212 or by detecting an eye blink of a predetermined duration. The highlighting may include changing a fill color or pattern of the selected plane, or changing the border color or style (e.g., dots, dashes, or hashes) of the selected plane.

Figure 2C:
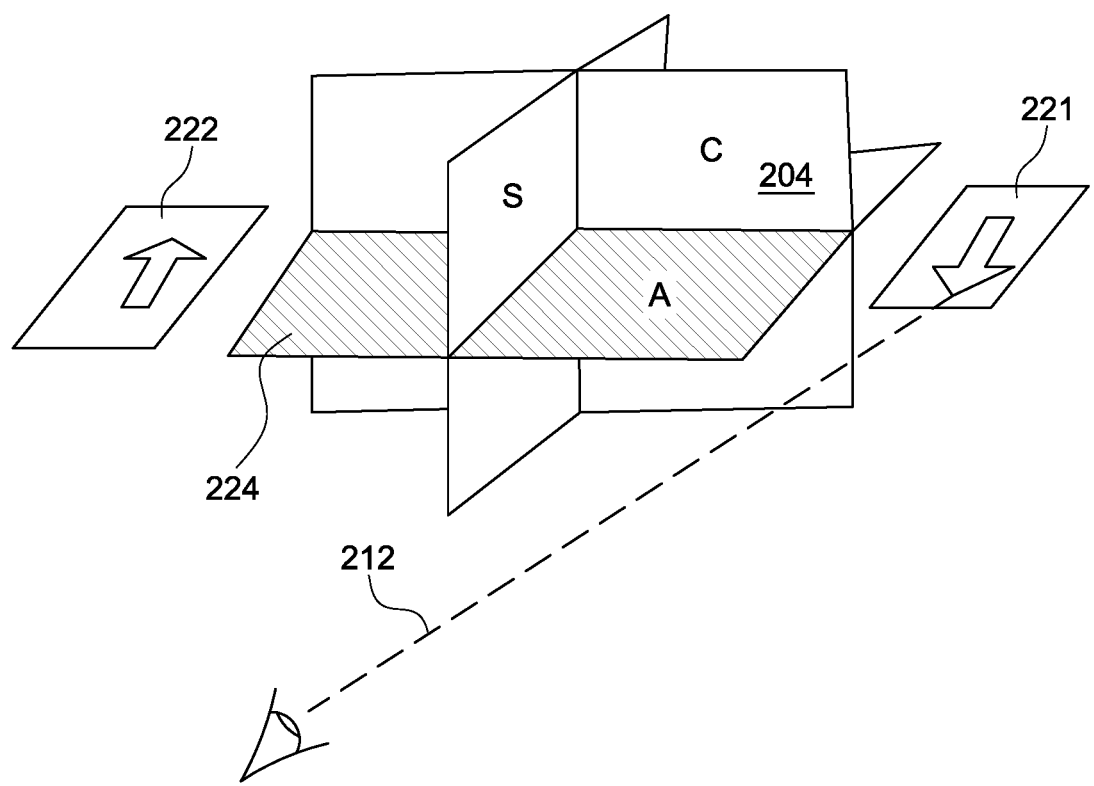

After a plane is selected, a forward control button 221 and a backward control button 222 are displayed in the headset display 116, as illustrated in FIG. 2C. In some aspects, the selected plane may remain highlighted while the forward control button 221 and the backward control button 222 are displayed. Additionally, or alternatively, an up control button and a down control button may be displayed in the headset display 116. In aspects, the control buttons 221, 222 may operate as auto-repeat buttons, which, when continuously selected by the surgeon's gaze, cause a selected plane to move until the focus of the surgeon's gaze is removed from one of the control buttons 221, 222. When the focus of the surgeon's gaze 212 is on the forward control button 221 for a predetermined period or greater, the selected plane 202 moves in the backward direction as indicated by the arrow displayed on the backward control button 221. Similarly, when the focus of the surgeon's gaze is on the backward control button 221 for a predetermined period or greater, the selected plane moves in the backward direction as indicated by the arrow displayed on the backward control button 221. In some aspects, the forward and backward control buttons 221, 222 may have positions and/or orientations different from the positions and/or orientations illustrated in FIG. 2C. For example, the forward and backward control buttons 221, 222 may be positioned adjacent to each other below the patient scan 115 or may be oriented parallel to the coronal plane 204.

The forward and backward control buttons 221, 222 shown in FIG. 2C are intended to be illustrative examples of control objects that may be controlled by a user's eyes via an eye tracker to manipulate patient scans 115 or a model displayed by the AR headset 110. For example, the control objects may include virtual joysticks, selectable buttons or icons, and scroll bars, which may be positioned and/or oriented in a manner suitable for manipulating the patient scans 115 or model displayed by the AR headset 110.

In some aspects, the selected plane may, at first, move at a slow rate and then accelerate up to a predetermined maximum acceleration rate as the focus of the surgeon's gaze is continuously held one of the control buttons 221, 222. The acceleration rate may be linear or may change in steps (e.g., 1×, 2×, 5×, 10×) where the focus time at each step may be a set amount (e.g., five seconds of continuous focus increases the step size). The selected plane in FIG. 2C may move accordingly to provide visual feedback to the surgeon on, for example, direction and current body location.

Figure 3:
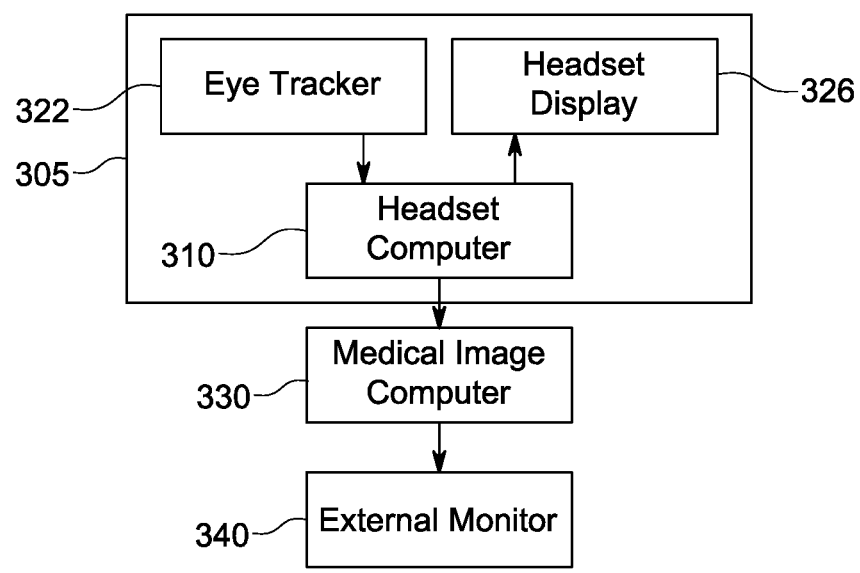
FIG. 3 is a block diagram of an augmented reality system according to aspects of the disclosure.

Referring now to FIG. 3, it may not be practical for the headset computer 304 to display medical images on the headset display 326 because of the low resolution of the headset display 326. Additionally, the contrast of the headset display 326 may be neither sufficient to occlude background interference (e.g., that which is outside of the headset 305 that would be behind the headset display 326) nor sufficient to overcome bright lights such as operating room lights. To address those issues, when the system is initially started, the medical image computer 330 notifies the headset computer 310 of the positional information (e.g., available planes, planes displayed, current position of each plane) of the scan currently displayed on the OR display or other external display. The headset computer 310 then constructs a local view of scan information currently displayed on the external monitor 340, which includes at least a representation of the scan information currently displayed on the external monitor 340.

Once the local view is constructed, the headset computer 310 can communicate control messages or commands to the medical image computer 330 based on user input or commands provided by the user's eyes via the eye tracker 322. For example, the headset computer 310 can communicate commands to scroll the displayed scan information and to add or delete planes of the displayed scan information to the medical image computer 330. The medical image computer 330 then updates the external monitor 340 accordingly. When an external user, e.g., a user not wearing the AR headset 305, scrolls the displayed scan information using the medical image computer 330, the new scan information may be sent to the headset computer 310 in real-time to update the corresponding scan information displayed the headset display 326.

In aspects, the user input or command includes gazing on a button for switching between views, e.g., switching between a view including a 3D model and a view including one or more medical scans, e.g., CT or fluoroscopic scans. The views may be windows. If two or more views are displayed simultaneously, e.g., a 3D model is displayed in one view and one or more 2D medical images are displayed in one or more other views, the user may select a view to manipulate, e.g., to rotate or zoom, by gazing at the view for a predetermined period. Additionally, or alternatively, the user input may include moving the user's gaze in a particular direction, which, when detected by the eye tracker 322, may cause the views to change.

In aspects, the user's gaze and/or movement of the user's gaze is used to manipulate, e.g., to scroll, zoom, or rotate, a 3D model or one or more medical scans. For example, the user may gaze on a slider of a scroll or zoom bar displayed to the user through the AR headset 305 for a predetermined period to grab hold of the slider, and then the user may move the user's gaze to a desired position on the scroll or zoom bar to achieve a desired amount of scrolling or zooming. To let go of the slider, the user may quickly move their gaze away from the slider in a particular direction, e.g., in a direction substantially perpendicular to the orientation of the scroll or zoom bar.

As another example, a user may gaze at a position on an AR view of a 3D model, e.g., a 3D model of a lung, for a predetermined period to grab hold of that position of the AR view of the 3D model. Then, the user may move the user's gaze in a desired direction to rotate the AR view of the 3D model in that direction. In some aspects, a user may gaze at a position in the AR view of the 3D model for a predetermined period to cause a 2D medical image corresponding to that position to be displayed in the same and/or another AR view.

A manipulation mode for manipulating medical images or views, e.g., zooming or rotating medical images or views, may be enabled when a user gazes at a button for a predetermined period or when the user moves the user's gaze in a particular way, e.g., the user moves the user's gaze in one direction for greater than a predetermined distance and then in another direction for greater than a predetermined distance. When the manipulation mode is enabled, a menu of items, e.g., buttons and/or slide bars, may be displayed by the AR headset 305.

In some aspects, the AR headset 305 may display a virtual controller interface with one or more joysticks and/or buttons, e.g., direction buttons, which may be controlled by the user's gaze to control the navigation of a robotic medical device, e.g., a flexible robotic endoscope. In other aspects, a user may control the navigation of a robotic medical device by gazing at a particular destination in a 3D model displayed by the AR headset 305. The user may enable such a navigation mode by gazing at a button displayed by the AR headset 305.

The systems and methods of the disclosure may include the display and control of other medical information. For example, a pre-surgical plan, a surgical checklist, vital signs, medical equipment status (e.g. RF generator settings), insufflation status, or any combination of this information may be displayed on the external monitor 340.

Figure 4:
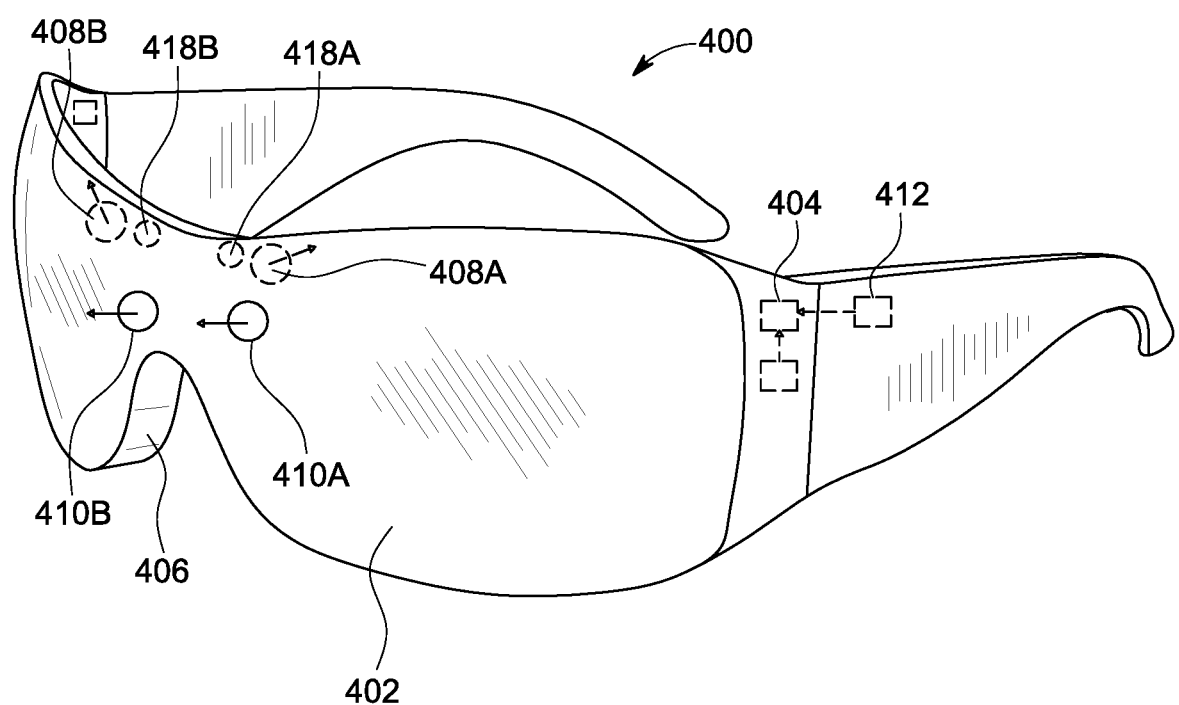
FIG. 4 is a perspective view of a head-mounted, see-through display device according to an aspect of the disclosure.

FIG. 4 shows an exemplary head-mounted display (HMD) 400, in the form of wearable glasses with a see-through display 402. For example, the HMD 400 may be a non-limiting example of the AR headset 110 of FIG. 1 and/or the AR headset 305 of FIG. 3. The HMD 400 may take any other suitable form in which a transparent, semi-transparent, and/or non-transparent display is supported in front of a viewer's eye or eyes. Further, implementations described herein may be used with any other suitable computing device, including but not limited to mobile computing devices, laptop computers, desktop computers, tablet computers, other wearable computers, etc.

The HMD 400 includes a see-through display 402, a controller 404, and a memory 412 connected to the controller 404. The controller 404 may be configured to perform various operations related to eye gaze detection or tracking, user input recognition, visual presentation of augmented-reality medical images on the see-through display 402, and other operations described herein.

The see-through display 402 may enable images such as augmented-reality images (also referred to as augmentation images or holograms) to be delivered to the eyes of a wearer of the HMD 400. The see-through display 402 may be configured to visually augment an appearance of a real-world, physical environment to a wearer viewing the physical environment through the see-through display 402. Any suitable mechanism may be used to display images via the see-through display 402. For example, the see-through display 402 may include image-producing elements located within lenses 406 (such as, for example, a see-through Organic Light-Emitting Diode (OLED) display). As another example, the see-through display 402 may include a display device (such as, for example, a liquid crystal on silicon (LCOS) device or OLED micro-display) located within a frame of HMD 400. In this example, the lenses 406 may serve as, or otherwise include, a light guide for delivering light from the display device to the eyes of a wearer. Such a light guide may enable a wearer to perceive a 3D holographic medical image located within the physical environment, e.g., operating room, that the wearer is viewing, while also allowing the wearer to directly view physical objects in the physical environment, thus creating a mixed-reality environment. Additionally, or alternatively, the see-through display 402 may present left-eye and right-eye augmented-reality images via respective left-eye and right-eye displays.

The HMD 400 may also include various sensors and related systems to provide information to the controller 404. Such sensors may include, but are not limited to, one or more inward facing image sensors 408A and 408B, and one or more outward facing image sensors 410A and 410B. The one or more inward facing image sensors 408A, 408B may be configured to acquire image data in the form of gaze tracking data from a wearer's eyes (e.g., sensor 408A may acquire image data for one of the wearer's eye and sensor 408B may acquire image data for the other of the wearer's eye). The controller 404 of the HMD 400 may be configured to determine gaze directions of each of a wearer's eyes in any suitable manner based on the information received from the image sensors 408A, 408B. For example, one or more light sources 418A, 418B, such as infrared light sources, may be configured to cause a glint of light to reflect from the cornea of each eye of a wearer. The one or more image sensors 408A, 408B may then be configured to capture an image of the wearer's eyes.

Images of the glints and of the pupils as determined from image data gathered from the image sensors 408A, 408B may be used by the controller 404 to determine an optical axis of each eye. Using this information, the controller 404 may be configured to determine a direction the wearer is gazing (also referred to as a gaze vector). The controller 404 may be configured to additionally determine an identity of a physical and/or virtual object at which the wearer is gazing by projecting the user's gaze vector onto a 3D model of the surrounding environment. The one or more light sources 418A, 418B, the one or more inward facing image sensors 408A, 408B, and the controller 404 may collectively represent to a gaze detector configured to determine a gaze vector of an eye of a wearer of the HMD 400.

In other implementations, a different type of gaze detector/sensor may be employed in the HMD 400 to measure one or more gaze parameters of the user's eyes. Examples of gaze parameters measured by one or more gaze sensors that may be used by the controller 404 to determine an eye gaze sample may include an eye gaze direction, head orientation, eye gaze velocity, eye gaze acceleration, change in angle of eye gaze direction, and/or any other suitable tracking information. In some implementations, eye gaze tracking may be recorded independently for both eyes of the wearer of the HMD 400. In one aspect, the controller 404 may determine if one of a left eye and a right eye of the user. These user-specific properties relating to the user's eyes can be used to increase the robustness and accuracy of eye tracking. For example, the eye tracking may place more weight on the eye tracking information obtained from the dominant eye.

Figure 5:
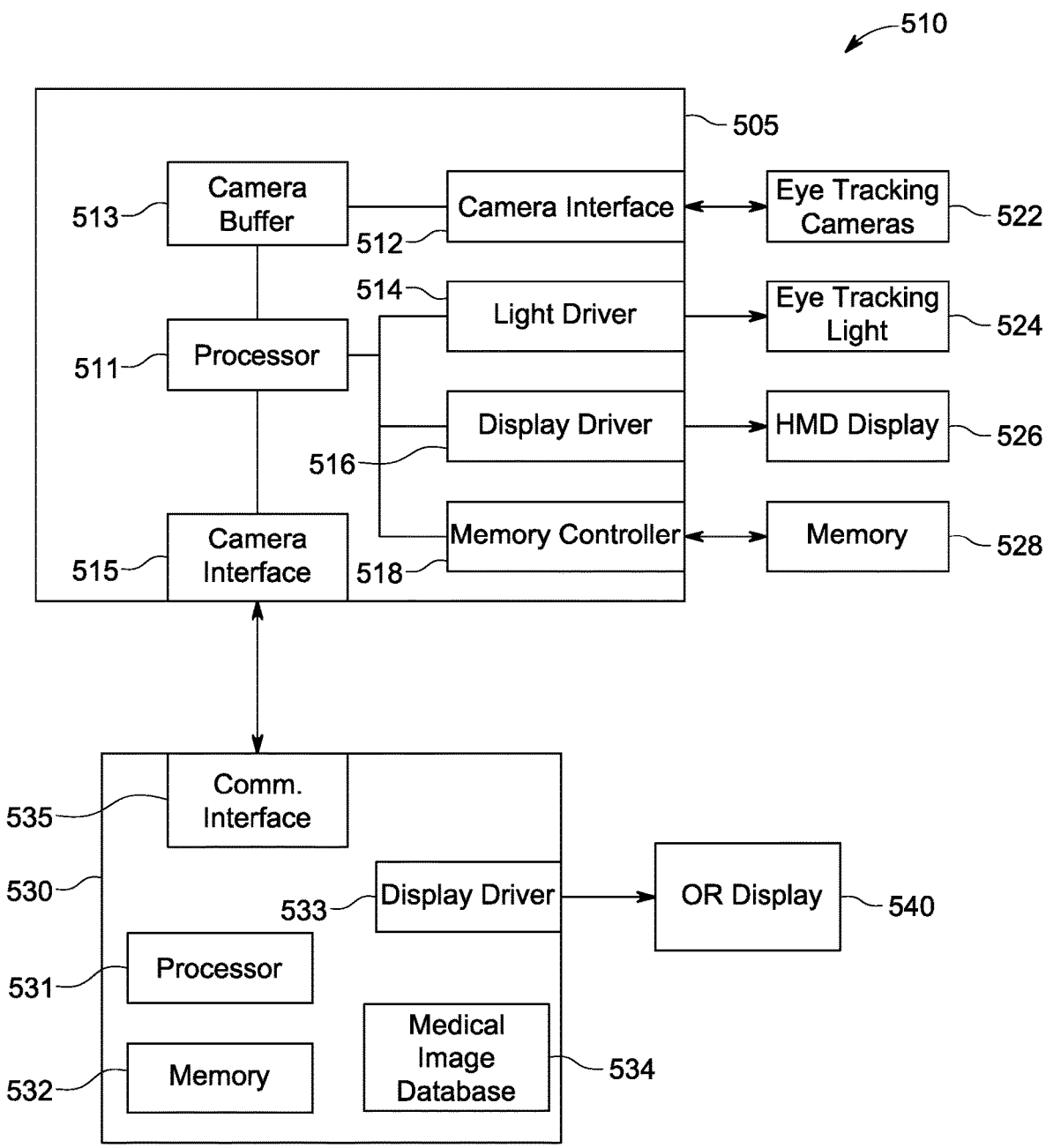
FIG. 5 is a block diagram of an operating room display system according to an aspect of the disclosure.
Figure 6:
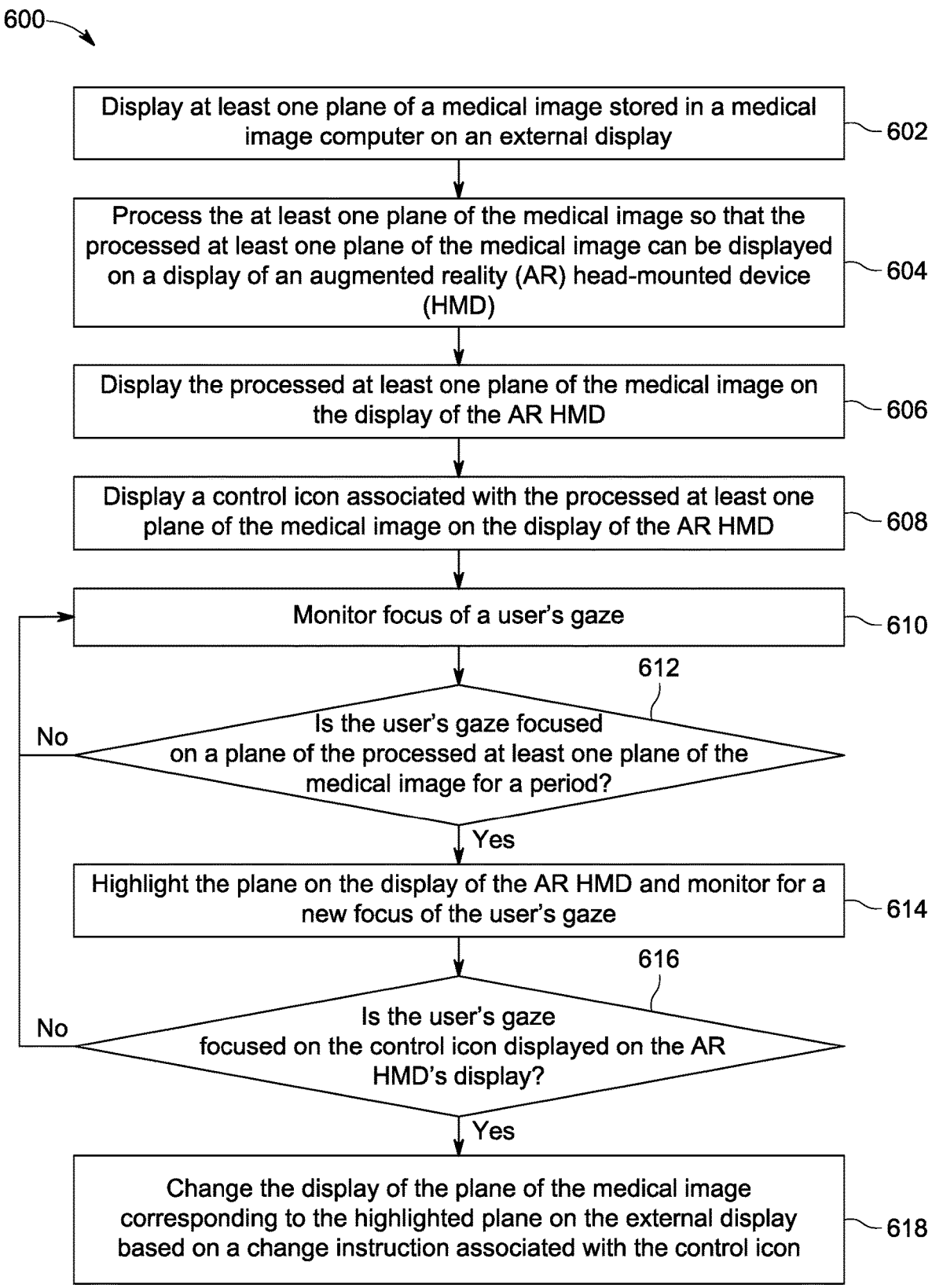
FIG. 6 is a flowchart of a method of controlling a medical image displayed on an external display by using an AR HMD according to an aspect of the disclosure.

Reference is now made to FIG. 5, which is a block diagram of an operating room display system configured for use with the methods of the disclosure including the method of FIG. 6. The operating room display system includes an augmented reality (AR) head mounted device (HMD) 510, a medical image computer 530 (also referred to as a workstation or an operating room computer), and an operating room (OR) display 540. The medical image computer 530 may be a stationary computing device, such as a personal computer, or a portable computing device such as a tablet computer.

The HMD 510 includes a control circuit 505, which may be in communication with a power management circuit (not shown) to manage the distribution and control of power to the components of the HMD 510. The control circuit 505 includes a processor 511, a memory controller 518 in communication with memory 528 (e.g., D-RAM), a camera interface 512, a camera buffer 513, a light driver 514 for driving an eye tracking light 524, and a display driver 516 for driving an HMD display 526. In one aspect, all of the components of the control circuit 505 are in communication with each other via dedicated lines of one or more buses, or using a shared bus. In another aspect, each of the components of the control circuit 505 is in communication with the processor 511.

The medical image computer 530 includes a processor 531, a memory 532, a display driver 533 for driving the operation of an OR display 540, a medical image database 534, and a communication interface 535, to enable the communication of medical images to the control circuit 505 of the HMD 510. Medical image computer 530 may optionally be connected to an imaging device, e.g., a computed tomography (CT) scanner, magnetic resonant imaging (MRI) scanner, a positron emission tomography (PET) scanner, or a fluoroscope. The imaging device may be connected to the medical image computer 530 directly or indirectly, e.g., by wireless communication. The processor 531 may include one or more processors. The memory 532 may store one or more applications and the medical image database 534 may store medical image data 1014. The one or more applications may include instructions executable by the processor 531 for executing the methods of the disclosure including executing a portion of the steps of the method of FIG. 6.

In some aspects, the medical image computer 530 may include an input device (not shown), which may be any device by which a user may interact with the medical image computer 530, such as, for example, a mouse, keyboard, foot pedal, touch screen, and/or voice interface. The medical image computer 530 may also include an output module (not shown). The output module may include any connectivity port or bus, such as, for example, parallel ports, serial ports, universal serial busses (USB), or any other similar connectivity port known to those skilled in the art.

The communications interfaces 515, 535 of the HMD 510 and the medical image computer 530 may be configured to connect to a network such as a local area network (LAN) consisting of a wired network and/or a wireless network, a wide area network (WAN), a wireless mobile network, a Bluetooth network, a cellular network, and/or the Internet. Communications interfaces 515, 535 may be used to establish a connection between the HMD 510 and the medical image computer 530. Communications interfaces 515, 535 may also be used to receive scan information including medical image data from an imaging device.

It should be appreciated by those skilled in the art that memory 528, 532 can be any media that can be accessed by the processors 511, 531. That is, the media may include non-transitory, volatile and non-volatile, removable and non-removable media implemented in any method or technology for storage of information such as computer-readable instructions, data structures, program modules or other data. For example, memory 532 may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by the processor 531.

Eye tracking cameras 522 can be used to detect eye elements such as a cornea center, a center of eyeball rotation and a pupil center for each eye. Based on such information, and/or other information obtained using the eye tracking cameras 522, the locations of a user's left and right eyes, including the interpupillary distance between the left and right eyes, can be determined. Additionally, the vertical positions of the left and right eyes relative to the HMD 510, and relative to one another, can be determined. The processor 511 can determine (e.g., calculate) the locations of the user's left and right eyes based on images and/or other information obtained by the eye tracking cameras 522.

The camera interface 512 provides an interface to the eye tracking cameras 522, which may include one or two outwardly facing cameras, and in an aspect, an IR camera. The camera interface 512 stores respective images received from the eye tracking cameras 522 in the camera buffer 513. The display driver 516 can drive an HMD display 526, e.g., a micro-display device or a see-through micro-display device. The control circuit 505 may include a display formatter (not shown), which may provide information about a virtual image being displayed on the HMD display 526 to one or more processors of one or more computer systems, e.g., the processor 531 of the medical image computer 530, performing processing for an augmented reality system.

FIG. 6 is a flowchart of a method 600 of controlling at least one plane of a medical image displayed on an external display by using an eye tracker and a display of an HMD according to an aspect of the disclosure. At block 602, at least one plane of a medical image stored in a medical image computer is displayed on an external display, which may be an operating room monitor. The external display may be an LED display, an OLED display, an LCD display, or any other display suitable for being viewed by a clinician within an operating room setting. The at least plane of the medical image may include one or more of an axial plane, a coronal plane, and a sagittal plane.

At block 604, the at least one plane of the medical image is processed so that the processed at least one plane of the medical image can be displayed on a display of an AR HMD. The processing may include image processing to reduce the resolution of the at least one plane of the medical image so that the display of the AR HMD is capable of displaying the at least one plane of the medical image. The processing may include other image processing to enable a clinician wearing the AR HMD to easily view the at least one plane of the medical image while also enabling the clinician to clearly see the surgical field through the AR HMD.

At block 606, the processed at least one plane of the medical image is displayed on the display of the AR HMD, and, at block 608, a control icon associated with the processed at least one plane of the medical image is also displayed on the display of the AR HMD. At block 610, a focus of a user's gaze is monitored, for example, by an eye tracker incorporated into the AR HMD. At block 612, the method 600 involves detecting whether the user's gaze is focused on a plane of the processed at least one plane of the medical image for a period. The period may be a predetermined period suitable for detecting that the user desires to select the plane. For example, the predetermined period may be between 3 seconds and 7 seconds. The predetermined period may also be adjustable by the user. If the user's gaze is focused on the plane for the period, the plane is highlighted on the display of the AR HMD. This indicates to the user the plane the user desires to control, e.g., move or scroll.

At block 614, after the plane is highlighted on the display of the AR HMD, a new focus of the user's gaze is monitored. At block 616, the method 600 involves detecting whether the user's gaze is focused on the control icon displayed on the AR HMD's display. If the user's gaze is focused on the control icon displayed on the AR HMD's display, the display of the plane of the medical image corresponding to the highlighted plane is changed on the external display based on a change instruction associated with the control icon. The change instruction may include an instruction to zoom in on or rotate the plane of the medical image on the external display.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A method comprising:
   displaying three-dimensional (3D) medical scan information of a portion of a patient in 3D space on an operating room display;
   communicating planes of the 3D medical scan information displayed on the operating room display to an augmented reality (AR) head-mounted device (HMD) configured to be mounted on a head of a user;
   displaying, on a display of the AR HMD, the planes of the 3D medical scan information perpendicular to one another, yielding perpendicular planes;
   monitoring a location of a focus of a user's gaze;
   updating the perpendicular planes of the 3D medical scan information on the operating room display based on monitored movement of the location of the focus of the user's gaze;
   detecting that the user's gaze is focused on a perpendicular plane of the perpendicular planes of the 3D medical scan information;
   in response to detecting that the user's gaze is focused on the perpendicular plane of the 3D medical scan information, highlighting the perpendicular plane of the 3D medical scan information, yielding a highlighted perpendicular plane of the 3D medical scan information, and displaying control objects associated with the highlighted perpendicular plane of the 3D medical scan information;

detecting that the user's gaze is focused on a control object of the control objects; and in response to detecting that the user's gaze is focused on the control object, determining selection of the control object and modifying the highlighted perpendicular plane of the 3D medical scan information in a way defined by the control object, wherein displaying the control objects associated with the highlighted perpendicular plane of the 3D medical scan information includes displaying movement direction control objects on opposite sides of the highlighted perpendicular plane of the 3D medical scan information, and wherein the movement direction control objects include up and down control objects and forward and backward control objects.

2. The method of claim 1, further comprising:
detecting that the user's gaze is focused on the control object;
in response to detecting that the user's gaze is focused on the control object, determining that the user's gaze satisfies a predetermined condition; and
in response to determining that a characteristic associated with the user's gaze satisfies a predetermined condition, recording selection of the control object.

3. The method of claim 2, wherein determining that a characteristic associated with the user's gaze satisfies a predetermined condition includes determining that the user's gaze is maintained for greater than a predetermined period.

4. The method of claim 2, wherein determining that a characteristic associated with the user's gaze satisfies a predetermined condition includes determining that the user blinks for greater than a predetermined period.

5. The method of claim 4, further comprising in response to recording the selection of the control object, displaying at least one perpendicular plane of the 3D medical scan information in place of the control object displayed on the display of the AR HMD.

6. The method of claim 1, further comprising continuously displaying at least one perpendicular plane of the 3D medical scan information on the display of the AR HMD.

7. The method of claim 6, further comprising determining a number of perpendicular planes of the 3D medical scan information that are currently displayed on the operating room display,
wherein the at least one perpendicular plane of the 3D medical scan information is displayed on the display of the AR HMD based on the number of perpendicular planes of the 3D medical scan information.

8. The method of claim 6, further comprising determining a number of perpendicular planes of the 3D medical scan information that are currently available to be displayed,
wherein the at least one perpendicular plane of the 3D medical scan information is displayed on the display of the AR HMD based on the number of perpendicular planes of the 3D medical scan information.

9. The method of claim 1, wherein the 3D medical scan information includes computed tomography (CT) scan information, magnetic resonant imaging (MRI) scan information, positron emission tomography (PET) scan information, or any combination thereof.

10. The method of claim 2, wherein the control object is a virtual joystick, a scrollbar, a button, or a selectable icon.

11. The method of claim 1, wherein highlighting the perpendicular plane of the 3D medical scan information includes changing a fill color, a fill pattern, a border color, or a border style of the perpendicular plane of the 3D medical scan information.

12. The method of claim 1, further comprising:
detecting that the user's gaze is focused on the control object; and
in response to detecting that the user's gaze is focused on the control object, determining selection of the control object and moving the highlighted perpendicular plane of the 3D medical scan information in a direction associated with the selection of the control object.

13. The method of claim 1, wherein the highlighted perpendicular plane of the 3D medical scan information is moved at a predetermined rate;
determining a length of time of detecting that the user's gaze is focused on the control object; and
increasing a movement rate at which the highlighted perpendicular plane of the 3D medical scan information is moved based on the length of time,
wherein increasing the movement rate includes increasing the movement rate linearly or in predetermined steps.

14. The method of claim 1, wherein displaying the 3D medical scan information includes displaying a three-dimensional (3D) model constructed based on medical scans, further comprising:
detecting that the user's gaze is focused on a portion of the 3D model; and
in response to detecting that the user's gaze is focused on the portion of the 3D model, displaying a perpendicular plane of the 3D medical scan information corresponding to the portion of the 3D model.

15. The method of claim 2, wherein the control objects include a slider of a scrollbar, further comprising:
detecting movement of the user's gaze to another position on the scrollbar; and
displaying a perpendicular plane of the 3D medical scan information corresponding to the another position on the scrollbar.

16. A system comprising:
an operating room (OR) monitor configured to display three-dimensional (3D) medical scan information of a portion of a patient in 3D space; and
an interactive head-mounted device (HMD) in communication with the OR monitor, the interactive HMD including:
an optical assembly configured to display medical images and to enable viewing of at least a portion of a surrounding environment;
an eye tracking device configured to track a location of a focus of a user's gaze; and
a processor in communication with the optical assembly and the eye tracking device; and
a memory configured to store an application, which, when executed by the processor, causes the processor to:
display 3D medical scan information on the OR monitor;
communicate planes of the 3D medical scan information displayed on the OR monitor to an interactive HMD configured to be mounted on a head of a user;
display, on the interactive HMD, the planes of the 3D medical scan information perpendicular to one another, yielding perpendicular planes;
monitor a location of a focus of a user's gaze;

update the perpendicular planes of the 3D medical scan information on the OR monitor based on monitored movement of the location of the focus of the user's gaze;

detect that the user's gaze is focused on a perpendicular plane of the perpendicular planes of the 3D medical scan information;

in response to detecting that the user's gaze is focused on the perpendicular plane of the 3D medical scan information, highlight the perpendicular plane of the 3D medical scan information, yielding a highlighted perpendicular plane of the 3D medical scan information, and display control objects associated with the highlighted perpendicular plane of the 3D medical scan information;

detect that the user's gaze is focused on a control object of the control objects; and in response to detecting that the user's gaze is focused on the control object, determine selection of the control object and modify the highlighted perpendicular plane of the 3D medical scan information in a way defined by the control object, wherein displaying the control objects associated with the perpendicular plane of the 3D medical scan information includes displaying movement direction control objects on opposite sides of the perpendicular plane of the 3D medical scan information, and wherein the movement direction control objects include up and down control objects and forward and backward control objects.

* * * * *